United States Patent [19]

Mantulo et al.

[11] 4,357,213

[45] Nov. 2, 1982

[54] METHOD OF RECOVERY OF LIQUID CHLORINE DERIVATIVES OF HYDROCARBONS

[76] Inventors: Alexandr P. Mantulo, ulitsa Kibalchicha, 14, kv. 118; Ivan N. Novikov, ulitsa A.Malyshko, 19a, kv. 57; Isai N. Feldman, prospekt Korneichuka, 38a, kv. 62, all of Kiev, U.S.S.R.

[21] Appl. No.: 188,545

[22] Filed: Sep. 18, 1980

[51] Int. Cl.[3] .......................... B01D 1/22; B01D 3/02

[52] U.S. Cl. ............................ 203/89; 159/DIG. 33; 203/100

[58] Field of Search ............................ 203/89, 42–46, 203/99, 100, 7, 11; 202/236, 168–170; 570/178, 238, 262; 159/5, 13 R, 13 A, 13 B, 13 C, 14, 15, DIG. 9, DIG. 17, DIG. 33

[56] References Cited

U.S. PATENT DOCUMENTS

| | | | |
|---|---|---|---|
| 2,514,944 | 7/1950 | Ferris et al. | 203/89 |
| 3,400,754 | 9/1968 | Barbu et al. | 203/7 |
| 3,409,511 | 11/1968 | Recheier et al. | 203/42 |
| 3,634,200 | 1/1972 | Obrecht et al. | 203/89 |
| 3,642,583 | 2/1972 | Greenberg et al. | 203/11 |
| 4,121,978 | 10/1978 | Becuwe | 570/262 |

*Primary Examiner*—Frank Sever

*Attorney, Agent, or Firm*—Lilling & Greenspan

[57] ABSTRACT

A method for recovering liquid chlorine derivatives of hydrocarbons resides in applying the chlorine derivatives of hydrocarbons to the preheated surface of an inert liquid, the temperature of the inert liquid exceeding the boiling temperature of the chlorine derivatives of hydrocarbons.

8 Claims, No Drawings

METHOD OF RECOVERY OF LIQUID CHLORINE DERIVATIVES OF HYDROCARBONS

BACKGROUND OF THE INVENTION

1. Field of the Invention

The present invention relates to a method for recovering liquid chlorine derivatives of hydrocarbons, and namely to a method for recovering chlorine derivatives of hydrocarbons from difficultly volatile impurities such as residues of a Friedel-Crafts catalyst, and resinous substances.

Chlorine derivatives of hydrocarbons are widely used as both solvents and intermediates in organic synthesis. Heavy demands are placed upon chlorine derivatives of hydrocarbons with respect to the content of catalytically active impurities and resinous substances. Therefore providing methods for recovering chlorine derivatives of hydrocarbons, ensuring a high quality of the end product is an important problem.

2. Description of the Prior Art

Known in the art is a method for recovering methyl chloroform (see British Pat. No. 930,172) comprising a Friedel-Crafts catalyst. This method for recovering methyl chloroform is carried out in a reactor wherein water is fed which is then heated to a temperature of 85° C. Thereafter methyl chloroform and ammonia are fed into the reactor, the ammonia being in an amount of 0.004 to 0.006 parts by weight per 1 part by weight of methyl chloroform. Shortly after being introduced into the 85° C. water, the methyl chloroform, having a boiling temperature of 74.1° C., soon boils. In the course of the recovery process, ferric chloride and hydrogen chloride contained in the methyl chloroform react with ammonia, and the vapors of methyl chloroform are condensed at a pH being within the range of 6 to 12. The condensate is then dried and rectified.

However, the use of the above method causes the wetting of the recovered methyl chloroform and its contamination with ammonia, which makes it necessary to later purify the methyl chloroform of ammonia.

In another method described in F.R.G Patent No. 1,235,878 ammonia is again used to purify methyl chloroform of catalysts. Known in the art is a method of purifying liquids of difficultly volatile impurities by distillation (A. G. Kasatkin, Osnovnye protsessy i apparaty khimicheskoi tekhnologii, Moskva, Khimia Publishers, 1971, pp. 393–397, 496–546). The recovery process resides in that the liquid containing difficultly volatile impurities is heated in a reaction vessel up to the boiling temperature of the end product. In so doing the liquid being recovered evaporates, the vapors pass through a condenser and condense therein, and the condensate is collected in a receptacle. The difficultly volatile impurities remain in the reaction vessel.

However, the above-described method involves prolonged heating of the liquid being recovered, which leads to decomposition of the end product. In addition, heating the liquids in the presence of catalyst residues leads to an increase in the amount of resinous substances. In view of the fact that the boiling temperature of the resinous substances is appreciably higher than that of the product being recovered, and both the liquid being recovered and the resinous substances are mutually soluble, the increase in the degree of evaporation requires that the temperature within the reactor be considerably higher than the boiling temperature of the end product. This will lead to a higher extent of decomposition of the substance being recovered and to an increase in the amount of resinous substances. The term "degree of evaporation" is used herein to denote the amount of the evaporated product and the initial amount of the product.

The method can also be carried out by evaporating a liquid from a film of an inert liquid. When using rotary film-type evaporators, the degree of evaporation increases. However, in this case the residue left after the distillation process comprising bottoms of a catalyst and resinous substances is a viscous resin which adheres to the evaporator surface on which evaporation of the liquid being recovered occurs. This leads to an uncontrollable increase in the thermal resistance of the heat exchange surface. In addition, the procedure of cleaning the heating surface from residues of a catalyst and resin is complicated and labor-consuming.

The principal object of the present invention is to provide a method of recovery of liquid chlorine derivatives of hydrocarbons which makes it possible to reduce the degree of decomposition of a product being recovered and at the same time to reduce the residues of catalyst and resinous substances.

SUMMARY OF THE INVENTION

These and other objects are attained by a method for recovering of liquid chlorine derivatives of hydrocarbons residing in distilling the chlorine derivatives of hydrocarbons, wherein, according to the invention, the chlorine derivatives of hydrocarbons are applied to the preheated surface of an inert liquid whose temperature exceeds the boiling temperature of the chlorine derivatives of hydrocarbons.

The term "inert liquid" is used herein to denote a chemically and physically inert liquid, i.e. a liquid which does not react with the components of the product being recovered and does not initiate chemical and physical changes therein.

The proposed method rids the liquid chlorine derivatives of hydrocarbons from difficultly volatile impurities, provides for a high degree of removal of the liquid chlorine derivatives from the product treated, and prevents contaminating of the heat-exchange surface of the evaporator by the residue resulting from the distillation process. Removal of the difficultly volatile impurities and separation of same from the inert liquid present no difficulties. In addition, contamination of the product by the inert liquid is avoided.

The result is attained due to a higher degree of removal of the volatile chlorine derivatives of hydrocarbons and due to a lower degree of thermal decomposition of the product being recovered owing to the stable conditions of heating the same product.

It is advisable that the chlorine derivatives of hydrocarbons be applied in the form of a thin layer to a film of an inert liquid continuously removed from the distillation zone. Such a modification of the method makes it possible to provide for the maximum yield of the product per unit area of the evaporator heat-exchange surface with maximum removal of difficultly volatile impurities and minimum resinification of the product being recovered.

It is expedient that used as an inert liquid be hexachlorobutadiene, or triethylene glycol, or trichlorodiphenyl, or polyphenyl methyl siloxane, or a perfluorocarbon liquid containing perfluorocarbons with the number of carbon atoms varying from $C_{14}$ to $C_{30}$. This modification of the method makes it possible to efficiently recover the chlorine derivatives of hydrocarbons and to obtain a high degree of recovery of the products insofar as the content of difficultly volatile impurities (residues of the catalyst and resinous substances) is concerned.

The chlorine derivatives of hydrocarbons may be applied in the form of a thin layer to a film of an inert liquid continuously removed from the distillation zone. The inert liquid may be an organic substance selected from the group consisting from hexachlorobutadiene, triethylene glycol, trichlorodiphenyl, polyphenyl methyl siloxane, and perfluorocarbon liquid containing perfluorocarbons with the number of carbon atoms varying from $C_{14}$ to $C_{30}$. This modification of the method makes it possible to obtain the maximum of the highly recovered product per unit area of the evaporator heat-exchange surface.

DETAILED DESCRIPTION OF THE INVENTION

Liquid chlorine derivatives of hydrocarbons, such as raw 1,1,1-trichloroethane, dichloromethane, raw 1,1-dichloroethane, raw 2-chlorobutane, are recovered in an apparatus comprising an evaporating flask, a settling tank, a circulating pump, a condenser, and a receptacle for the recovered product. The central neck the evaporating flask is provided with a blade stirrer with a disk feeder mounted on the same shaft as the blades of the stirrer but higher than these blades. The evaporating flask is also provided with a neck for feeding a liquid chlorine derivative of a hydrocarbon therethrough and into the evaporating flask, with a neck for feeding an inert liquid into the evaporating flask, and with a neck for discharging the inert liquid together with separated residues of the catalyst into the settling tank. The inert liquid may be hexachlorobutadiene, or triethylene glycol, or trichlorodiphenyl, or polyphenyl methyl siloxane, or a perfluorocarbon liquid containing perfluorocarbons with the number of carbon atoms varying from $C_{14}$–$C_{30}$.

The inert liquid is circulated within the "evaporating flask—settling tank—evaporating flask" system by means of a circulating pump.

Prior to the recovery process, adequate temperature conditions are provided within the flask. For this purpose, the evaporating flask with an inert liquid is placed in a liquid bath, such as a glycerin bath, and the contents of the evaporating flask are heated to a temperature exceeding the boiling temperature of the liquid chlorine derivative of hydrocarbon. Then a stirrer is actuated at a speed of 2.5 to 3.5 r.p.s. to form the surface of the inert liquid into a depression cone, so that the upper boundary of the cone reaches the neck for discharging the inert liquid from the evaporating flask into the settling tank. The circulating pump is brought into operation to enable the inert liquid to continuously circulate through the evaporating flask and the settling tank. Thereafter, the liquid chlorine derivative of hydrocarbon is fed into the evaporating flask through one of its necks and by means of the disk feeder applied to the surface of the inert liquid. The chlorine derivative of hydrocarbon evaporates from the surface of the inert liquid and passes into the condenser, whereas the inert liquid together with the separated difficultly volatile impurities passes from the evaporating flask into the settling tank.

After condensation, the recovered chlorine derivative of hydrocarbon is collected in the receptacle, and the inert liquid is separated from the difficultly volatile impurities and returned to the evaporating flask.

The liquid chlorine derivatives of hydrocarbons may also be recovered by an apparatus comprising a rotary film-type evaporator, a circulating pump, a heater for heating an inert liquid, a condenser, and a receptacle for the recovered product, and a settling tank. The settling tank, pump and the receptacle for the recovered product are disposed lower than the rotary film-type evaporator.

The rotary film-type evaporator is made from an alloyed steel and is 450 mm in height and 40 mm in its internal diameter. The speed of the rotor is 180 r.p.m. The evaporator is provided in its upper portion with 3 branch pipes: (1) for feeding an inert liquid thereto; (2) for feeding the liquid chlorine derivative of a hydrocarbon for recovery; (3) for removing vapors recovered from the chlorine derivative of a hydrocarbon. In the bottom portion of the evaporator there is disposed a branch pipe for removing an inert liquid and difficultly volatile impurities. The evaporator is also provided with bosses to introduce thermocouples for controlling the temperature of the inert liquid recovered. In the upper portion of the rotor there are means for a uniform distribution of the inert liquid over the whole surface of the evaporator. These means may be in the form of blades or in any other suitable form.

In the above-described apparatus, chlorine derivatives of hydrocarbons are recovered in the following way. A heat carrier, such as steam, is fed into the jacket of the evaporator. An inert liquid is fed into the evaporator. Then the rotor is brought into operation, and the circulating pump enables the inert liquid to circulate within the "evaporator—settling tank—evaporator" system. A chlorine derivative of a hydrocarbon being recovered is continuously fed through the upper pipe onto the surface of the inert liquid wherefrom it evaporates.

In the recovery process, the vapors of the chlorine derivative of a hydrocarbon pass into the condenser through the pipe of the evaporator, whereas the inert liquid and difficultly volatile impurities are continuously removed from the evaporator into the settling tank where the inert liquid is separated from the difficultly volatile impurities. From the settling tank the inert liquid which is now free from the difficultly volatile impurities, is continuously fed into the upper portion of the evaporator by the circulating pump.

Described above were methods for continuous recovery of liquid chlorine derivatives of hydrocarbons. However, the recovery process may be carried out periodically as well. In the latter case, an inert liquid is poured into the reactor and heated, whereupon a product to be recovered is added approximately to the central portion of the reactor. The feeding rate of the chlorine derivative of a hydrocarbon is varied so that its layer on the surface of the inert liquid does not contact the walls of the reactor. Vapors of the chlorine derivative of a hydrocarbon are condensed and the obtained distillate is accumulated in the receptacle for the recovered product. The inert liquid together with the difficultly volatile impurities are discharged from the reactor at the end of the recovery process.

The recovered chlorine derivative of a hydrocarbon was tested to determine the content of residues of the catalyst and resinous substances therein as well as the degree of decomposition. The testing was carried out in accordance with conventional procedures.

EXAMPLE 1

A method for recovering liquid chlorine derivatives of hydrocarbons according to the invention was carried out in the following way.

Hexachlorobutadiene in an amount of 129 g was charged into an evaporating flask and heated in a glycerin bath up to a temperature of 100° C., whereupon a stirrer was brought into operation at a speed of 2.5 r.p.s to form the surface of hexachlorobutadiene into a depression cone to allow the upper boundary of the cone to reach a branch pipe for discharging hexachlorobutadiene from the evaporating flask into a circulation loop "evaporating flask—settling tank—evaporating flask". A circulating pump was brought into operation.

Thereafter raw 1,1,1-trichloroethane in an amount of 250 g was delivered to a disk feeder within 4.5 hours, the composition of the raw 1,1,1-trichloroethane being the following, % by mass:

| | |
|---|---|
| $CH_3—CCl_3$ | |
| $CH_2═CCl_2$ | |
| $CH_3—CHCl_2$ | |
| trans-$CHCl═CHCl$ | |
| $CH_2Cl—CH_2Cl$ | |
| $CH_2CHCl_2$ | |
| resinous substances | 0.2 |
| catalyst residue | 0.25 |
| acid content (calculated as HCl) | 0.13 |
| moisture content in the product being recovered | $5 \cdot 10^{-4}$ |

The raw 1,1,1-trichloroethane being recovered was sprayed onto a constantly moving film of hexachlorobutadiene. This being the case, 1,1,1-trichloroethane evaporated from the film, whereas the catalyst and the resinous substances were mixed with hexachlorobutadiene and passed from the evaporating flask into the settling tank through the branch pipe.

After condensation, the 1,1,1-trichloroethane was accumulated in a receptacle for the recovered product, whereas hexachlorobutadiene, partially liberated in the settling tank from the catalyst and the resinous substances, was pumped back into the evaporating flask. As a result, 205 g of recovered raw 1,1,1-trichloroethane was obtained which was tested to determine the decomposition degree thereof as well as the residual content of impurities therein.

The results of the testing were as follows:

| | |
|---|---|
| residual content of impurities, in % by mass: | |
| catalyst | $6 \cdot 10^{-3}$ |
| resinous substances | $5 \cdot 10^{-3}$ |
| moisture content in the recovered product | $5 \cdot 10^{-4}$ |

EXAMPLE 2

A method for recovering liquid chlorine derivatives of hydrocarbons according to the invention was carried out in the following way.

Triethylene glycol in an amount of 156 g was charged into an evaporating flask and heated in a glycerin bath up to a temperature of 102° C., whereupon a stirrer was brought into operation at a speed of 3.5 r.p.s. to form the surface of triethylene glycol into a depression to allow the upper boundary of the cone to reach the branch pipe for discharging triethylene glycol from the evaporating flasks into the cylindrical loop "evaporating flask—settling tank—evaporating flask". A circulating pump was brought into operation.

Thereafter raw 1,1,1-trichloroethane in an amount of 280 g was delivered to a disk feeder within 5 hours, the composition of the raw 1,1,1-trichloroethane being the following, % by mass:

| | |
|---|---|
| $CH_3—CCl_3$ | |
| $CH_2═CCl_2$ | |
| $CH_3—CHCl_2$ | |
| trans $CHCl═CHCl$ | |
| $CH_2Cl—CH_2Cl$ | |
| $CH_2Cl—CHCl_2$ | |
| resinous substances | |
| catalyst residue ($FeCl_3$) | 0.25 |
| acid content (calculated as HCl) | 0.13 |
| moisture content in the product being recovered | $5 \cdot 10^{-4}$ |

Raw 1,1,1-trichloroethane being recovered was sprayed onto a continuously moving film of triethylene glycol. This being the case, 1,1,1-trichloroethane evaporated from the film, whereas the residue of the catalyst and the resinous substances mixed with triethylene glycol passed from the evaporating flask into the settling tank through the branch pipe.

After condensation, the 1,1,1-trichloroethane was accumulated in a receptacle for the recovered product, whereas triethylene glycol, partially liberated from the catalyst and the resinous substances in the settling tank, were pumped back into the evaporating flask. As a result, there was obtained 240 g of recovered 1,1,1-trichloroethane which was tested to determine the degree of decomposition thereof as well as the residual content of impurities therein. The results of the testing were as follows:

| | |
|---|---|
| degree of decomposition of 1,1,1-trichloroethane | 12.0% |
| residual content of impurities, in % by mass: | |
| catalyst residue ($FeCl_3$) | $4 \cdot 10^{-3}$ |
| resinous substances | $5 \cdot 10^{-3}$ |
| moisture content in the recovered product | $5 \cdot 10^{-4}$ |

EXAMPLE 3

A method for recovering liquid chlorine derivatives of hydrocarbons according to the invention was carried out in the following way.

Trichlorodiphenyl in an amount of 119 g and containing 42% by mass of chlorine was charged into an evaporating flask and heated in a glycerin bath to a temperature of 110° C., whereupon a stirrer was brought into operation at a speed of 3.5 r.p.s. to form the surface of trichlorodiphenyl into a depression cone to allow the upper boundary of the cone to reach the branch pipe for discharging trichlorodiphenyl from the evaporating flask into a circulation loop. A circulating pump was brought into operation.

Thereafter raw 1,1,1-trichloroethane in an amount of 300 g was delivered to a disk feeder within 5.5 hours, the composition of raw 1,1,1-trichloroethane being the following, % by mass:

| | |
|---|---|
| $CH_3—CCl_3$ | |
| $CH_2=CCl_2$ | |
| $CH_3—CHCl_2$ | |
| trans-$CHCl=CHCl$ | |
| cis-$CHCl=CHCl$ | |
| $CH_2Cl—CH_2Cl$ | |
| $CH_2Cl—CHCl_2$ | |
| resinous substances | 0.2 |
| catalyst residue ($FeCl_3$) | 0.2 |
| acid content (calculated as HCl) | $5 \cdot 10^{-4}$ |
| moisture content in the product being recovered | $5 \cdot 10^{-4}$ |

Raw 1,1,1-trichloroethane being recovered was sprayed onto a continuously moving film of trichlorodiphenyl. This being the case, 1,1,1-trichloroethane evaporated from the film, whereas the residue of the catalyst and the resinous substances mixed with trichlorodiphenyl passed from the evaporating flask through a branch pipe into a settling tank.

After condensation, 1,1,1-trichloroethane was accumulated in a receptacle for the recovered product, whereas trichlorodiphenyl, partially liberated from the catalyst and the resinous substances in a settling tank, was pumped back into the evaporating flask. There was obtained 238 g of recovered raw 1,1,1-trichloroethane which was tested to determine the decomposition degree thereof as well as the residual content of impurities therein.

The results of the testing were as follows:

| | |
|---|---|
| degree of decomposition of 1,1,1-trichloroethane | 6.8% |
| residual content of impurities, % by mass: | |
| catalyst residue | $5 \cdot 10^{-3}$ |
| resinous substances | $8 \cdot 10^{-3}$ |
| moisture content in the recovered product | $5 \cdot 10^{-4}$ |

EXAMPLE 4

A method for recovering liquid chlorine derivatives of hydrocarbons according to the invention was carried out in the following way.

A perfluorocarbon liquid in an amount of 212 g was charged into an evaporating flask. The perfluorocarbon liquid was a mixture of aliphatic perfluorocarbons with the number of carbon atoms varying from $C_{14}$ to $C_{30}$ having a boiling temperature of 95% mass thereof being 190° C. at 10 mm Hg, the viscosity at a temperature of 100° C. being 500 cP, and the density being 2000 kg/m$^3$.

The evaporating flask was heated up to a temperature of 80° C., whereupon a stirrer was brought into operation at a speed of 5 r.p.s. to form the surface of the perfluorocarbon liquid into a depression cone to allow the upper boundary of the cone to reach the branch pipe for discharging this inert liquid from the evaporating flask into the circulation loop. A circulation pump was brought into operation.

Thereafter raw 1,1,1-trichloroethane in an amount of 168 g was delivered to a disk feeder within 3 hours, the components of raw 1,1,1-trichloroethane being taken in the following amounts, % by mass:

-continued

| | |
|---|---|
| $CH_3—CCl_3$ | |
| $CH_2=CCl_2$ | |
| $CH_3—CHCl_2$ | |
| trans-$CHCl=CHCl$ | |
| $CH_2Cl—CH_2Cl$ | |
| $CH_2Cl—CHCl_2$ | |
| resinous substances | 0.2 |
| catalyst residue ($FeCl_3$) | 0.25 |
| acid content (calculated as HCl) | 0.13 |
| moisture content in the product being recovered | $1 \cdot 10^{-4}$ |

Raw 1,1,1-trichloroethane being recovered was sprayed onto a continuously moving film of the perfluorocarbon liquid. This being the case 1,1,1-trichloroethane evaporated from the surface of this hydrocarbon, whereas the residue of the catalyst and the resinous substances mixed with the perfluorocarbon liquid, after passing from the evaporating flask was separated from the hydrocarbon by settling.

After condensation, 1,1,1-trichloroethane was accumulated in a receptacle for the recovered product, whereas aliphatic perfluorocarbon liberated from the catalyst and the resinous substances in a settling tank was pumped back into the evaporating flask. There was obtained 162 g of recovered 1,1,1-trichloroethane which was tested to determine the decomposition degree thereof as well as the residual content of impurities therein.

The results of the testing were as follows:

| | |
|---|---|
| degree of decomposition of 1,1,1-trichloroethane | 1.4% |
| residual content of impurities, % by mass: | |
| catalyst residue | less than $1 \cdot 10^{-3}$ |
| resinous substances | less than $1 \cdot 10^{-3}$ |
| moisture content in the product being recovered | $1 \cdot 10^{-4}$ |

EXAMPLE 5

A method for recovering liquid chlorine derivatives of hydrocarbons according to the invention was carried out in the following way.

A perfluorocarbon liquid similar to that of Example 4 was charged in an amount of 212 g into an evaporating flask, whereupon a stirrer was brought into operation at a speed of 3.5 r.p.s. to form the surface of the perfluorocarbon liquid into a depression cone to allow the upper boundary of the cone to reach the branch pipe for discharging this product from the evaporating flask into the circulation loop. A circulation pump was brought into operation.

Thereafter raw 1,1,1-trichloroethane in an amount of 680 g was delivered to a disk feeder within 3 hours, the composition of raw 1,1,1-trichloroethane being the following, % by mass:

| | |
|---|---|
| $CH_3—CCl_3$ | |
| $CH_2=CCl_2$ | |
| $CH_3—CHCl_2$ | |
| trans-$CHCl=CHCl$ | |
| $CH_2Cl—CH_2Cl$ | |
| $CH_2Cl—CHCl_2$ | |
| resinous substances | 0.2 |
| catalyst residue ($FeCl_3$) | 0.25 |
| acid content (calculated as HCl) | 0.13 |
| moisture content in the product being recovered | $1 \cdot 10^{-4}$ |

1,1,1-trichloroethane being recovered was sprayed onto a continuously moving film of the perfluorocarbon liquid. This being the case, 1,1,1-trichloroethane evaporated from the surface of this hydrocarbon liquid, whereas the residue of the catalyst and the resinous substances mixed with said perfluorocarbon liquid, after passing from the evaporating flask was separated from said perfluorocarbon liquid by settling.

After condensation, 1,1,1-trichloroethane was accumulated in a receptacle for the recovered product, whereas the perfluorocarbon liquid liberated from the catalyst and the resinous substances in a settling tank was pumped back into the evaporating flask. There was obtained 665 g of recovered 1,1,1-trichloroethane which was tested to determine the decomposition degree thereof as well as the residual content of impurities therein.

The results of the testing were as follows:

| | |
|---|---|
| degree of decomposition of 1,1,1-trichloroethane | 2.1% |
| residual content of impurities, % by mass: | |
| catalyst residue | less than $1 \cdot 10^{-3}$ |
| resinous substances | less than $1 \cdot 10^{-3}$ |
| moisture content in the recovered product | $1 \cdot 10^{-4}$ |

EXAMPLE 6

A method of recovery of liquid chlorine derivatives of hydrocarbons according to the invention was carried out in the following way.

Polyphenyl methyl siloxane in an amount of 160 g was charged into an evaporating flask and heated in a glycerin bath to a temperature of 70° C., whereupon a stirrer was brought into operation at a speed of 3.5 r.p.s. to form the surface of polyphenyl methyl siloxane into a depression cone to allow the upper boundary of the cone to reach the branch pipe for discharging polyphenyl methyl siloxane into the circulation loop "evaporating flask—settling tank—evaporating flask". A circulation pump was brought into operation.

Thereafter dichloromethane in an amount of 450 g was delivered within 3 hours onto a disk feeder. The composition of dichloromethane was the following, % by mass:

| | |
|---|---|
| $CH_2Cl_2$ | |
| cis + trans-CHCl═CHCl | |
| $CH_3$—$CHCl_2$ | |
| $CHCl_3$ | |
| acid content (calculates as HCl) | 0.05 |
| moisture content in the product recovered | $8 \cdot 10^{-3}$ |
| non-volatile impurities containing, in addition to resinous substances, $Fe^{+3}$, $Fe^{+2}$ | 0.1 |

Dichloromethane being recovered was sprayed onto a continuously moving film of polyphenyl methyl siloxane. This being the case, dichloromethane evaporated from the film, whereas the residues of the catalyst, and the non-volatile products mixed with polyphenyl methyl siloxane, passed from the evaporating flask to the settling tank through the branch pipe.

After condensation, dichloromethane was accumulated in a receptacle for the recovered product, whereas polyphenyl methyl siloxane liberated from the non-volatile impurities and the resinous substances in the settling tank was pumped back into the evaporating flask. There was obtained 406 g of recovered dichloromethane which was tested to determine the decomposition degree thereof as well as the residual content of impurities therein.

The results of the testing were as follows:

| | |
|---|---|
| degree of decomposition of dichloromethane | 0.7% |
| residual content of non-volatile impurities containing, in addition to resinous substances, $Fe^{+3}$, $Fe^{+2}$, % by mass | $1 \cdot 10^{-3}$ |
| moisture content | $5 \cdot 10^{-3}$ |
| acid content (calculated as HCl) | $6 \cdot 10^{-2}$ |

EXAMPLE 7

A method for recovering liquid chlorine derivatives of hydrocarbons according to the invention was carried out in the following way.

A perfluorocarbon liquid in an amount of 210 g was charged into an evaporating flask and heated up to a temperature of 80° C., whereupon a stirrer was brought into operation at a speed of 2.0 r.p.s. to form the surface of the perfluorocarbon liquid into a depression cone to allow the upper boundary of the cone to reach a branch pipe for discharging perfluorocarbon from the evaporating flask into the circulation loop "evaporating flask—settling tank—evaporating flask". A circulation pump was brought into operation.

Thereafter raw 1,1,-dichloroethane in an amount of 170 g was delivered to a disk feeder within 2 hours. The composition of raw 1,1-dichloroethane was, % by mass:

| | |
|---|---|
| $CH_3$—$CHCl_2$ | |
| $CH_2$═CHCl | |
| CHCl═CHCl | |
| $CH_2Cl$—$CHCl_2$ | |
| resinous substances | 0.6 |
| residual content of catalyst ($AlCl_3$) | 0.2 |
| HCl | 0.5 |

Raw 1,1-dichloroethane was sprayed onto a continuously moving film of the perfluorocarbon liquid. This being the case, 1,1-dichloroethane evaporated from the film, whereas the residues of the catalyst and the resinous substances mixed with the perfluorocarbon liquid passed from the evaporating flask through the branch pipe into the settling tank.

After condensation, 1,1-dichloroethane free from the residues of the catalyst and the resinous substances was accumulated in a receptacle for the recovered product, whereas the perfluorocarbon liquid liberated from the catalyst and the resinous substances in the settling tank was pumped back into the evaporating flask. There was obtained 166 g of recovered 1,1-dichloroethane which was tested to determine the decomposition degree thereof as well as the residual content of impurities therein.

The results of the testing were as follows:

| | |
|---|---|
| degree of decomposition, % | 0 |
| residual content of impurities, % by mass: | |
| catalyst ($AlCl_3$) | $2 \cdot 10^{-3}$ |

-continued

| | |
|---|---|
| resinous substances | $1 \cdot 10^{-3}$ |

EXAMPLE 8

A method for recovering liquid chlorine derivatives of hydrocarbons according to the invention was carried out in the following way.

Raw 1,1,1-trichloroethane was recovered in an apparatus comprising a rotary film-type evaporator, settling tank, circulating pump, heater for heating an inert liquid, condenser, and a receptacle for the recovered product. Prior to the recovery process, steam having a temperature of 125° C. was fed to the jacket of the rotary film-type evaporator. The engine was actuated which brought the rotor into operation. With the aid of the circulating pump a perfluorocarbon liquid was caused to circulate in the system "evaporator—settling tank—heater—evaporator". This liquid was a mixture of aliphatic perfluorocarbons with the number of carbon atoms varying from 15 to 25. The boiling temperature of the 95% mass of this liquid was 190° C. at 10 mm Hg, the viscosity was 500 cP at a temperature of 100° C., and the density was 2,000 kg/m$^3$. The flow rate of the liquid was 60 kg/hr. When the temperature of the perfluorocarbon liquid was as high as 108° C., a continuous feeding of 1,1,1-trichloroethane started through the upper branch, said 1,1,1-trichloroethane comprising, % by mass:

| | |
|---|---|
| $CH_3$—$CCl_3$ | |
| $CH_2$=$CCl_2$ | |
| $CH_3$—$CHCl_2$ | |
| trans-CHCl=CHCl | |
| cis-CHCl=CHCl | |
| $CH_2Cl$—$CH_2Cl$ | |
| $CH_2Cl$—$CHCl_2$ | |
| resinous substances | 0.2 |
| residual content of catalyst ($FeCl_3$) | 0.25 |
| acid content (calculated as HCl) | 0.15 |

The flow rate of 1,1,1-trichloroethane was 185 kg/hr.

In the course of recovery, the perfluorocarbon liquid and the residues resulting from the distillation process and comprising resinous substances and a catalyst were continuously removed from the evaporator into the settling tank where the resinous substances and the catalyst were separated from the perfluorocarbon liquid which is always at the bottom portion of the settling tank. From the settling tank the perfluorocarbon liquid free from impurities was continuously pumped to the upper portion of the evaporator. Vapors of 1,1,1-trichloroethane having a temperature of 74° C. passed through a branch pipe of the evaporator into the condenser.

1,1,1-trichloroethane recovered as described above was tested to determine the decomposition degree, the content of resinous substances, the moisture content in the recovered product, the residual content of ferric chloride in the recovered product, the content of dissolved hydrogen chloride, and the degree of evaporation.

The obtained results were as follows:

| | |
|---|---|
| decomposition degree, % | 2.0 |
| moisture content, % by mass | $1 \cdot 10^{-3}$ |
| residual content of ferric chloride calculated as $Fe^{+3}$, % by mass | $1.10^{-4}$ |
| residual content of dissolved hydrogen chloride, % by mass | $6 \cdot 10^{-1}$ |
| content of resinous substances, % by mass | $5 \cdot 10^{-5}$ |
| evaporation degree | 250:1 |

1,1,1-trichloroethane was also recovered in a conventional way, following the above conditions. In this case 1,1,1-trichloroethane evaporated on the surface of the evaporator. Thus recovered 1,1,1-trichloroethane was tested to determine the decomposition degree, the residual content of ferric chloride in the recovered product, the evaporation degree.

The obtained results were as follows:

| | |
|---|---|
| decomposition degree, % | 2.99 |
| content of resinous substances, % by mass | $5 \cdot 10^{-3}$ |
| residual content of ferric chloride calculated as $Fe^{+3}$, % by mass | $2 \cdot 10^{-3}$ |
| evaporation degree | 100:1 |

EXAMPLE 9

A method for recovering liquid chlorine derivatives of hydrocarbons according to the invention was carried out in the following way.

Raw 2-chlorobutane was recovered in an apparatus comprising a rotary film-type evaporator, settling tank, circulating pump, heater for heating an inert liquid, condenser, and a receptacle for the recovered product. Prior to the recovery process, steam having a temperature of 125° C. was fed to the jacket of the rotary film-type evaporator. The engine was actuated which brought the rotor into operation. With the aid of the circulating pump a perfluorocarbon liquid was caused to circulate in the system "evaporator—settling tank—heater—evaporator". This liquid was a mixture of aliphatic perfluorocarbons with the number of carbon atoms varying from 14 to 30 and was characterized by the following parameters: the boiling temperature of the 95% mass of the same liquid was 190° C. at 10 mm Hg, the viscosity was 500 cP at a temperature of 100° C., and the density was 2,000 kg/m$^3$.

The flow rate of the liquid was 1.0 g/min.

When the temperature of the perfluorocarbon liquid was as high as 108° C., raw 2-chlorobutane was fed through the upper branch pipe, said 2-chlorobutane being of the following composition, % by mass:

| | |
|---|---|
| $CH_3CH(Cl)$—$CH_2$—$CH_3$ | 97.0 |
| isomeric products | 2.0 |
| $FeCl_3$ | 0.3 |
| resinous substances | 0.5 |
| HCl | 0.2 |
| 205 g 2-chlorobutane was recovered within 1 hour. | |

Decomposition of 2-chlorobutane was not observed.

EXAMPLE 10

A method for recovering liquid chlorine derivatives of hydrocarbons according to the invention was carried out in the following way.

Raw 1,1,1-trichloroethane was recovered in an apparatus comprising a rotary film-type evaporator, settling tank, circulating pump, heater for heating an inert liquid, condenser, and a receptacle for the recovered product.

Prior to the recovery process, steam having a temperature of 125° C. was fed into the jacket of the rotary film-type evaporator. The engine was actuated which brought the rotor into operation. With the aid of the circulating pump an inert liquid was caused to circulate in the system "evaporator—settling tank—heater—evaporator". The inert liquid was a perfluorocarbon liquid comprising a mixture of liquid aliphatic perfluorocarbons with the number of carbon atoms varying from $C_{14}$ to $C_{30}$. The perfluorocarbon liquid has a boiling temperature of a 95% mass thereof equal to 190° C. at 10 mm Hg, the viscosity at a temperature of 100° C., 300 cP, the density, 2,000 kg/m$^3$. The flow rate of the inert liquid was 45 kg/hr. When the temperature of said perfluorocarbon liquid was as high as 110° C., 1,1,1-trichloroethane was fed through the upper branch pipe, said 1,1,1-trichloroethane comprising in % by mass:

| | |
|---|---|
| $CH_3$—$CCl_3$ | |
| $CH_2$=$CCl_2$ | |
| $CH_3$—$CHCl_2$ | |
| trans-CHCl=CHCl | |
| cis-CHCl=CHCl | |
| $CH_2Cl$—$CH_2Cl$ | |
| $CH_2Cl$—$CHCl_2$ | |
| resinous substances | 0.2 |
| residual content of catalyst ($FeCl_3$) | 0.25 |
| acid content (calculated as HCl) | 0.15 |

The flow rate of 1,1,1-trichloroethane was 123 kg/hr.

In the course of recovery, the perfluorocarbon liquid and the residues resulting from the distillation process and comprising resinous substances and a catalyst were continuously removed from the evaporator into the settling tank where the resinous substances and the catalyst were separated from the perfluorocarbon liquid. From the settling tank the perfluorocarbon liquid free from impurities was continuously pumped into the upper portion of the evaporator. Vapors of 1,1,1-trichloroethane having a temperature of 74° C. passed through a branch pipe of the evaporator into the condenser.

The recovered 1,1,1-trichloroethane was tested to determine the decomposition degree, the content of resinous substances, and the residual content of ferric chloride.

There were obtained the following results:

| | |
|---|---|
| decomposition degree, % | 4.0 |
| residual content of catalyst ($FeCl_3$), % by mass | $1 \cdot 10^{-3}$ |
| content of resinous substances, % by mass | $1 \cdot 10^{-3}$ |

EXAMPLE 11

A method for recovering liquid chlorine derivatives of hydrocarbons according to the invention was carried out in the following way.

Raw 1,1,1-trichloroethane was recovered in an apparatus comprising a rotary film-type evaporator, settling tank, circulating pump heater for heating an inert liquid, condenser, and a receptacle for the recovered product.

Prior to the recovery process, steam having a temperature of 125° C. was fed into the jacket of the rotary film-type evaporator. The engine was actuated which brought the rotor into operation. With the aid of the circulating pump an inert liquid was caused to circulate in the system "evaporator—settling tank—heater—evaporator". The inert liquid was a perfluorocarbon liquid comprising a mixture of liquid aliphatic perfluorocarbons with the number of carbon atoms varying from $C_{14}$ to $C_{30}$. The perfluorocarbon liquid has the boiling temperature of 95% mass thereof equal to 190° C. at 10 mm Hg, the viscosity at a temperature of 100° C., 300 cP, the density, 2,000 kg/m$^3$. The flow rate of the inert liquid was 30 kg/hr. When the temperature of said perfluorocarbon liquid was as high as 108° C., 1,1,1-trichloroethane was fed through the upper branch pipe, said 1,1,1-trichloroethane comprising in % by mass:

| | |
|---|---|
| $CH_3$—$CCl_3$ | |
| $CH_2$=$CCl_2$ | |
| $CH_3$—$CHCl_2$ | |
| trans-CHCl=CHCl | |
| cis-CHCl=CHCl | |
| $CH_2Cl$—$CH_2Cl$ | |
| $CH_2Cl$—$CHCl_2$ | |
| resinous substances | 0.2 |
| residual content of catalyst ($FeCl_3$) | 0.3 |
| acid content (calculated as HCl) | 0.12 |

The flow rate of 1,1,1-trichloroethane was 185 kg/hr.

In the course of recovery, the perfluorocarbon liquid and the residues resulting from the distillation process and comprising resinous substances and a catalyst were continuously removed from the evaporator into the settling tank where the resinous substances and the catalyst were separated from the perfluorocarbon liquid. From the settling tank the perfluorocarbon liquid free from impurities was continuously pumped into the upper portion of the evaporator. Vapors of 1,1,1-trichloroethane having a temperature of 74° C. passed through a branch pipe of the evaporator into the condenser. The recovered 1,1,1-trichloroethane was tested to determine the decomposition degree, the content of resinous substances, the residual content of ferrous chloride.

There were obtained the following results:

| | |
|---|---|
| decomposition degree, % | 2.0 |
| residual content of catalyst ($FeCl_3$), % by mass | $7 \cdot 10^{-4}$ |
| content of resinous substances, % by mass | $1 \cdot 10^{-3}$ |

EXAMPLE 12

A method for recovering liquid chlorine derivatives of hydrocarbons according to the invention was carried out in the following way.

The recovery process was carried out in an apparatus comprising a reactor, a condenser, and a receptacle. An inert liquid was poured into the reactor and heated up to a temperature exceeding the boiling temperature of the product to be recovered. Thereafter the product to be recovered was poured dropwise in approximately the central part of the surface of the inert liquid. The feeding rate of the chlorine derivative of hydrocarbon was varied so that its layer on the surface of the inert liquid did not contact the walls of the reactor. Vapors of the chlorine derivative of the hydrocarbon were condensed and the obtained distillate was accumulated in the receptacle.

The residue resulting from the distillation procedure remained in the reactor and on completion of the recovery process was removed therefrom.

Hexachlorobutadiene in an amount of 141 g was placed into the reactor and heated up to a temperature of 100° C., whereupon raw 1,1,1-trichloroethane in an amount of 180 g was fed for 4 hours, said 1,1,1-trichloroethane being of the following composition, % by mass:

| | |
|---|---|
| $CH_3$—$CCl_3$ | |
| $CH_2$=$CCl_2$ | |
| $CH_3$—$CHCl_2$ | |
| trans-CHCl=CHCl | |
| cis-CHCl=CHCl | |
| $CH_2Cl$—$CH_2Cl$ | |
| residual content of catalyst ($FeCl_3$) | 0.25 |
| resinous substances | 0.2 |
| acid content (calculated as HCl) | 0.13 |

There was obtained 138 g of the recovered chlorine derivative of the hydrocarbon containing ferric chloride in an amount of $7.10^{-3}$ % by mass and resinous substances in an amount of $5.10^{-3}$ % by mass.

EXAMPLE 13 (COMPARATIVE)

A recovery process was accomplished in an apparatus comprising a reactor, a condenser, and a receptacle. An inert liquid was poured into the reactor and heated up to a temperature exceeding the boiling temperature of a product to be recovered. Thereafter the product to be recovered was poured dropwise approximately to the central part of the surface of the inert liquid. The feeding rate of the chlorine derivative of the hydrocarbon was varied so that its layer on the surface of the inert liquid did not contact the walls of the reactor. Vapors of the chlorine derivative of the hydrocarbon were condensed and the obtained distillate was accumulated in the receptacle.

The residue resulting from the distillation procedure remained in the reactor and at the end of the recovery process was removed therefrom.

Ortho-chlorotoluene in an amount of 183 g was placed into the reactor and heated up to a temperature of 100° C., whereupon raw 1,1,1-trichloroethane in an amount of 150 g was fed for 3 hours, said 1,1,1-trichloroethane being of the following composition, % by mass:

| | |
|---|---|
| $CH_3$—$CCl_3$ | |
| $CH_2$=$CCl_2$ | |
| $CH_3$—$CHCl_2$ | |
| trans-CHCl=CHCl | |
| cis-CHCl=CHCl | |
| $CH_2Cl$—$CH_2Cl$ | |
| residual content of catalyst ($FeCl_3$) | 0.25 |
| resinous substances | 0.2 |
| acid content (calculated as HCl) | 0.13 |

There was obtained 94 g of the recovered chlorine derivative of the hydrocarbon containing ferric chloride in an amount of $6.10^{-3}$ % by mass, resinous substances in an amount of $6.10^{-3}$ % by mass, and ortho-chlorotoluene in an amount of 0.4% by mass.

Thus, the utilization of ortho-chlorotoluene as an inert liquid reduces the yield of the end product and leads to its contamination with ortho-toluene.

While particular embodiments of the invention have been shown and described, various modifications thereof will be apparent to those skilled in the art and therefore it is not intended that the invention be limited to the disclosed embodiments or to the details thereof and that departures may be made therefrom within the spirit and scope of the invention as defined in the claims.

What is claimed is:

1. A method for recovering liquid chlorine derivatives of hydrocarbons from an impure liquid containing impurities that are less volatile than said liquid chlorine derivatives, comprising: heating a second liquid which is chemically inert and has a substantially higher vapor pressure relative to said impure liquid, and in which said impurities are substantially soluble, to a temperature below the vaporization temperature of said impurities, but above the vaporization temperature of said derivatives, contacting said impure liquid with the surface said second liquid thereby recovering a substantially pure vapor of said derivatives, and substantially retaining the impurities in said second liquid.

2. The method of claim 1, wherein said inert liquid is an organic substance selected from the group consisting of hexachlorobutadiene, triethylene glycol, trichlorodiphenyl, polyphenyl methyl siloxane, and perfluorocarbon liquid containing perfluorocarbons with the number of carbon atoms varying from $C_{14}$ to $C_{30}$.

3. The method of claim 1, wherein said chlorine derivatives of hydrocarbons are applied in the form of a thin layer to a film of said inert liquid being continuously removed from the distillation zone.

4. The method of claim 3, wherein said inert liquid is an organic substance selected from a group consisting of hexachlorobutadiene, triethylene glycol, trichlorodiphenyl, polyphenyl methyl siloxane, and perfluorocarbon liquid containing perfluorocarbons with the number of carbon atoms varying from $C_{14}$ to $C_{30}$.

5. The method of claim 4, wherein the distillation occurs in a vessel containing the inert liquid stirred rapidly so that its surface forms a depression cone with an upper boundary overflowing said vessel at a predetermined rate.

6. A method for recovering a desired liquid component from an impure liquid containing impurities that are less volatile than said desired liquid component, comprising: heating a second liquid which is chemically inert and has a substantially higher vapor pressure relative to said impure liquid, impurities are substantially soluble, to a temperature below the vaporization temperature of said impurities, but above the vaporization temperature of said desired liquid component, contacting said impure liquid with the surface said second liquid, thereby recovering a substantially pure vapor of said desired liquid component, and substantially retaining the impurities in said second liquid.

7. The method of claim 6, wherein said impure liquid is in the form of a thin film contacting said inert liquid that is being continuously removed from the distillation zone.

8. The method of claim 6, wherein the distillation occurs in a vessel containing the inert liquid stirred rapidly so that its surface forms a depression cone with an upper boundary overflowing said vessel at a predetermined rate.

* * * * *